United States Patent
Hashimoto et al.

(10) Patent No.: US 9,085,596 B2
(45) Date of Patent: Jul. 21, 2015

(54) IRIDIUM COMPLEX AND ORGANIC LIGHT-EMITTING DEVICE CONTAINING SAME

(75) Inventors: Masashi Hashimoto, Tokyo (JP); Chiaki Nishiura, Kawasaki (JP); Shigemoto Abe, Yokohama (JP); Hiroya Nitta, Yokohama (JP); Isao Kawata, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 638 days.

(21) Appl. No.: 13/513,848

(22) PCT Filed: Nov. 26, 2010

(86) PCT No.: PCT/JP2010/071753
§ 371 (c)(1),
(2), (4) Date: Jun. 4, 2012

(87) PCT Pub. No.: WO2011/070990
PCT Pub. Date: Jun. 16, 2011

(65) Prior Publication Data
US 2012/0242255 A1   Sep. 27, 2012

(30) Foreign Application Priority Data
Dec. 8, 2009   (JP) .................................. 2009-278968

(51) Int. Cl.
*H01L 51/54* (2006.01)
*C09K 11/06* (2006.01)
*C07F 15/00* (2006.01)
*H01L 51/00* (2006.01)
*H01L 51/50* (2006.01)
*H05B 33/14* (2006.01)

(52) U.S. Cl.
CPC ............. *C07F 15/0033* (2013.01); *C09K 11/06* (2013.01); *H01L 51/0085* (2013.01); *H01L 51/5016* (2013.01); *H05B 33/14* (2013.01); *C09K 2211/1007* (2013.01); *C09K 2211/1029* (2013.01); *C09K 2211/1059* (2013.01); *C09K 2211/185* (2013.01)

(58) Field of Classification Search
None
See application file for complete search history.

(56) References Cited

U.S. PATENT DOCUMENTS

| 2003/0068536 | A1* | 4/2003 | Tsuboyama et al. | 428/704 |
| 2006/0127696 | A1* | 6/2006 | Stossel et al. | 428/690 |
| 2010/0019669 | A1* | 1/2010 | Akino et al. | 313/504 |

FOREIGN PATENT DOCUMENTS

| JP | 2003-515897 A | 5/2003 |
| JP | 2006-513278 A | 4/2006 |
| JP | 2008-179617 A | 8/2008 |
| WO | 01/08230 A1 | 2/2001 |
| WO | 2004/045000 A2 | 5/2004 |

* cited by examiner

*Primary Examiner* — Marie R. Yamnitzky
(74) *Attorney, Agent, or Firm* — Canon USA Inc. IP Division

(57) ABSTRACT

There is provided a new iridium complex including phenylpyridine as a ligand, the iridium complex having a basic skeleton in which a triazine ring is bonded to a phenyl ring.

10 Claims, 5 Drawing Sheets

IRIDIUM COMPLEX AND ORGANIC LIGHT-EMITTING DEVICE CONTAINING SAME

TECHNICAL FIELD

The present invention relates to a new iridium complex and an organic light-emitting device containing the iridium complex.

BACKGROUND ART

The development of organic light emitting elements has been intensively conducted. PTL 1 discloses $Ir(PPy)_3$. PTL 2 discloses $Ir(PPy)_2acac$.

[Chem. 1]

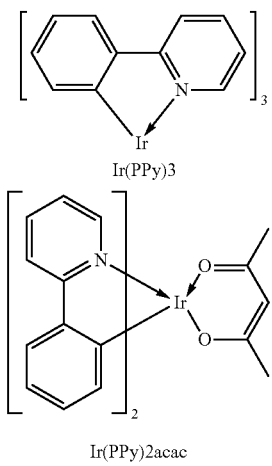

Ir(PPy)3

Ir(PPy)2acac

CITATION LIST

Patent Literature

PTL 1 WO2001/08230

PTL 2 PCT Japanese Translation Patent Publication No. 2003-515897

The compound $[Ir(PPy)_3]$ represented by the foregoing structural formula described in PTL 1 and the compound $[Ir(PPy)_2acac]$ represented by the foregoing structural formula described in PTL 2 emit green light. They are required to have improved emission characteristics.

Aspects of the present invention provide a new iridium complex having excellent emission characteristics in the blue-to-green region. Aspects of the present invention also provide an organic light-emitting device containing the iridium complex and having excellent emission characteristics.

SUMMARY OF INVENTION

Accordingly, one aspect of the present invention provides an iridium complex represented by formula (1):

[Chem. 2]

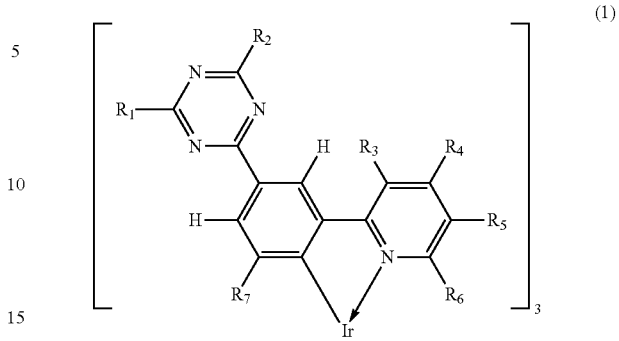

wherein $R_1$ and $R_2$ each independently represent an alkyl group; and $R_3$ to $R_7$ each independently represent one selected from a hydrogen atom, a cyano group, alkyl groups, alkoxy groups, and substituted amino groups.

Another aspect of the present invention provides an iridium complex represented by formula (2):

[Chem. 3]

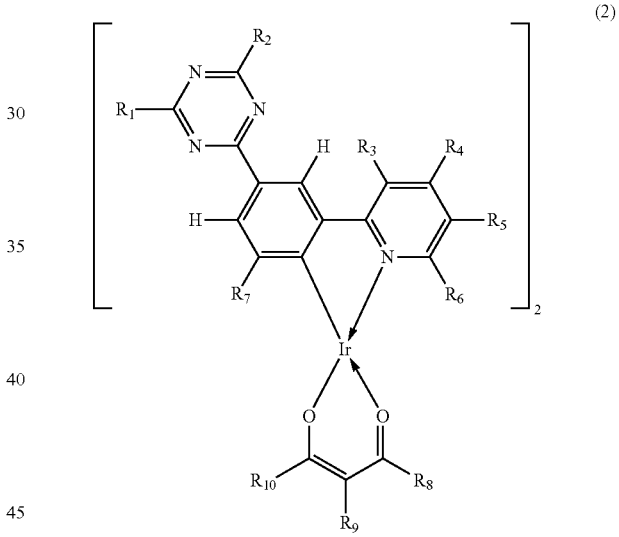

wherein $R_1$ and $R_2$ each independently represent an alkyl group; $R_3$ to $R_7$ each independently represent one selected from a hydrogen atom, a cyano group, alkyl groups, alkoxy groups, and substituted amino groups; and $R_8$ to $R_{10}$ each independently represent one selected from a hydrogen atom and alkyl groups.

DESCRIPTION OF EMBODIMENTS

Figure 1:
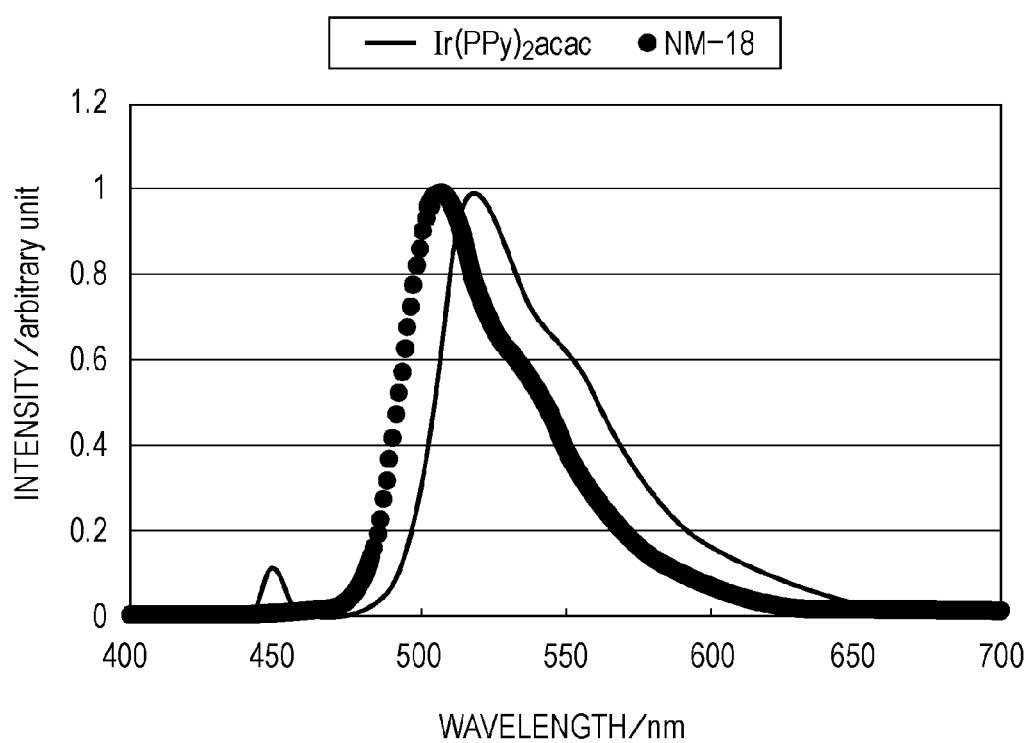
FIG. 1 illustrates emission spectra of exemplary compound MN-18 according to an embodiment and $Ir(PPy)_2acac$ according to a comparative example at room temperature.

An iridium complex according to aspects of the present invention is represented by formula (1) or (2) described below:

[Chem. 4]

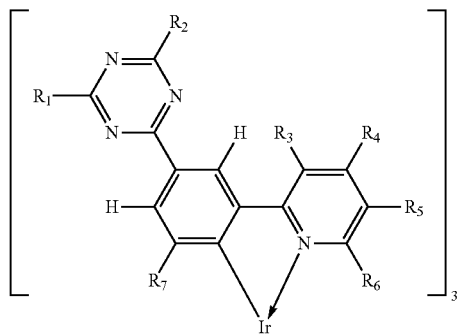

(1)

wherein H represents a hydrogen atom; N represents a nitrogen atom; Ir represents an iridium atom; $R_1$ and $R_2$ each independently represent an alkyl groups; and $R_3$ to $R_7$ each independently represent one selected from a hydrogen atom, a cyano group, alkyl groups, alkoxy groups, and substituted amino groups.

Examples of the alkyl group include methyl, ethyl, n-propyl, isopropyl, n-butyl, tert-butyl, adamantyl, octyl, and cyclohexyl groups.

Among these alkyl groups, a methyl group and tert-butyl group can be used from the viewpoint of achieving good conductivity and sublimability.

Examples of alkoxy groups include methoxy and ethoxy groups.

Among the substituted amino groups, a dimethylamino group can be used from the viewpoint of achieving good conductivity and sublimability.

The iridium complex represented by formula (1) according to aspects of the present invention has a triazine ring-phenyl ring-pyridine ring skeleton in which their rings are bonded at specific positions as illustrated in formula (1). Hereinafter, this skeleton is referred as the "main skeleton of the ligand of formula (1)".

The iridium complex according to aspects of the present invention is a superior ligand that emits blue or green light, owing to a strong ligand field resulting from the main skeleton of the ligand of formula (1).

The triazine ring-phenyl ring-pyridine ring ligand may have four structures of A to D described below. Structure C, i.e., the main skeleton of the ligand of formula (1), is a superior basic skeleton of a light-emitting material that emits light in a blue region.

[Chem. 5]

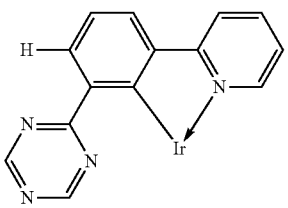

A

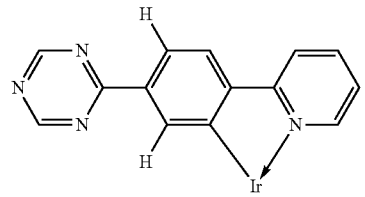

B

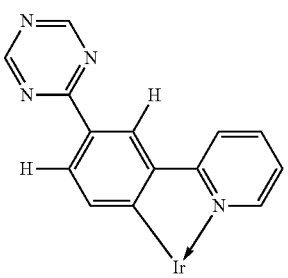

C

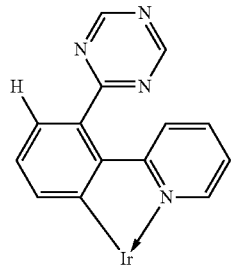

D

To achieve excellent emission characteristics in blue- and green-light-emitting regions, it is necessary to use a ligand that can form a stronger ligand field.

To increase the strength of the ligand field, it is important to maximize the π back-donation from iridium, which serves as the central metal, to the ligand. The π back-donation indicates that an electron is donated from the central metal of a complex to a ligand.

The inventors have found that the following two points are important to effectively enhance the effect of the π back-donation induced by the electron-withdrawing triazine ring. Each of structures A to D described above has iridium, the pyridine ring, the phenyl ring, and triazine ring.

1. The site of substitution of the triazine ring on the phenyl ring is the ortho-position or the para-position of the phenyl ring with respect to iridium.

2. The triazine ring and the phenyl ring are coplanar.

For structure B, iridium and the triazine ring are located at the meta-position of the phenyl ring, which does not satisfy the first requirement described above.

Furthermore, in each of structures A and D, the coplanar structure formed of the triazine ring and the phenyl ring is not maintained because of the steric repulsion between the triazine ring and the neighboring iridium atom for structure A and because of the steric repulsion between the triazine ring and the neighboring pyridine ring for structure D. Thus, structures A and D do not satisfy the second requirement.

Therefore, only structure C satisfies the first requirement and the second requirement. The main skeleton of the ligand of formula (1) is excellent in the blue-to-green region, in particular, in the blue region.

Furthermore, two H atoms of the phenyl ring, i.e., two H atoms in formula (1), are important in maintaining the coplanarity of the triazine ring and the phenyl ring.

Table 1 shows the dihedral angle between the triazine ring and the phenyl ring, the dihedral angle being determined by molecular orbital calculations.

TABLE 1

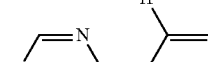

| Structural formula | (H, H pyrimidine-phenyl) | (F, F pyrimidine-phenyl) | (Me, Me pyrimidine-phenyl) |
|---|---|---|---|
| Dihedral angle between two rings | 0° | 43° | 50° |

As described above, the hydrogen atoms may be located at the neighboring positions of the triazine ring bonded to the phenyl ring in order to maintain the coplanarity of the two rings.

The dihedral angle in a ground state was determined by structural optimization calculations using Gaussian 03* Revision D.01, which is commercially available electronic-state computational software.

In this case, the density functional theory was used as a quantum chemical calculation method using the B3LYP functional with the 6-31G* basis set.

* Gaussian 03, Revision D.01,
M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

In formula (1), each of $R_1$ and $R_2$ may represent an alkyl group having a large excluded volume.

The reason for this is that the steric coverage of the lone pairs of the triazine ring can suppress the coordinating ability of the nitrogen atoms of the triazine ring. As a substituent having a large excluded volume, a substituent having tertiary carbon atom with $sp^3$ hybrid orbitals is effective. For example, a tert-butyl group or a 1-adamantyl group can be used.

The introduction of an alkyl group having a large excluded volume can lead to any one of the following effects.

1. It is possible to synthesize the high-purity complex in high yield.

2. The suppression of the coordinating ability of the nitrogen atoms leads to the inhibition of the trapping of ionic impurities by the lone pairs, improving the lifetime of the organic light-emitting device.

3. It is possible to inhibit intermolecular interactions to suppress concentration quenching of the light-emitting material. The concentration quenching is a phenomenon in which luminous efficiency is reduced at a high concentration.

$R_3$ may represent a substituent having a small excluded volume from the viewpoint of achieving the stability of the complex. The reason for this is as follows: $R_3$ is located in the sterically closest vicinity of the hydrogen atom of the phenyl ring. Large steric repulsion between $R_3$ and the hydrogen atom causes an increase in torsion angle between the phenyl ring and the pyridine ring. A large torsion angle results in an increase in the strain of the pyridine ring-iridium atom-phenyl ring bonds, thereby weakening the bond between the ligand and iridium. Thus, $R_3$ may represent a hydrogen atom. Each of $R_6$ and $R_7$ may represent a substituent having a small excluded volume from the viewpoint of achieving a high synthetic yield. Specifically, each of $R_6$ and $R_7$ may represent a hydrogen atom or a cyano group.

Furthermore, the iridium complex according to aspects of the present invention can be an iridium complex represented by formula (2):

[Chem. 6]

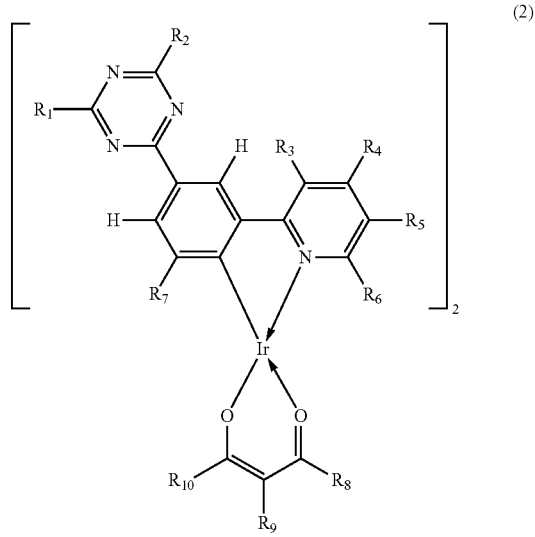

wherein $R_1$ to $R_7$ in formula (2) are defined the same as $R_1$ to $R_7$ in formula (1).

$R_8$ and $R_{10}$ each independently represent one selected from a hydrogen atom and alkyl groups.

Examples of the alkyl group include methyl, isopropyl, tert-butyl, octyl, and cyclohexyl groups. $R_8$ and $R_{10}$ may each independently represent an alkyl group from the viewpoint of achieving the stability of the compound. Among these alkyl groups, a methyl group or a tert-butyl group can be used from the viewpoint of achieving good conductivity and sublimability and inhibiting concentration quenching.

The iridium complex according to aspects of the present invention may be used as a guest material or a host material for a light-emitting layer of an organic light-emitting device. The organic light-emitting device includes a pair of electrodes facing each other, and a light-emitting layer provided between the electrodes. The organic light-emitting device may include another layer other than the light-emitting layer. The iridium complex according to aspects of the present invention may also be appropriately used for a layer other than the light-emitting layer, i.e., a hole injection layer, a hole transport layer, a hole exciton blocking layer, an electron transport layer, or an electron injection layer.

The term "host material" used here indicates a compound having the highest proportion in weight among compounds contained in the light-emitting layer. The term "guest material" indicates a compound having a lower proportion in weight than that of the host material among the compounds contained in the light-emitting layer.

The iridium complex according to aspects of the present invention can be used as the guest material for the light-emitting layer of the organic light-emitting device. In particular, the iridium complex can be used as the guest material for a blue- or green-light-emitting device.

The introduction of a substituent into the basic skeleton of the iridium complex according to aspects of the present invention makes it possible to change the emission wavelength.

In the case where the iridium complex according to aspects of the present invention is used as the guest material of the light-emitting layer, a material having a higher LUMO level than that of the iridium complex, i.e., a material having a LUMO level closer to the vacuum level, can be used as the host material. This is because the iridium complex according to aspects of the present invention has a low LUMO level and thus can successfully receive electrons from the light-emitting layer, i.e., the host material. The LUMO level is the abbreviation for the lowest unoccupied molecular orbital level. The HOMO level is the abbreviation for the highest occupied molecular orbital level. The host material and the guest material will be described in further detail below.

Illustration of Iridium Complex According to Aspects of the Present Invention

Specific examples of compounds represented by formulae (1) and (2) are illustrated below. The present invention is not limited thereto.

[Chem. 7]

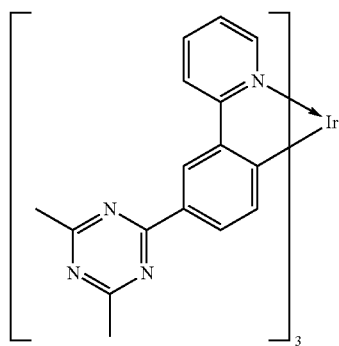

MN-1

[Chem. 8]

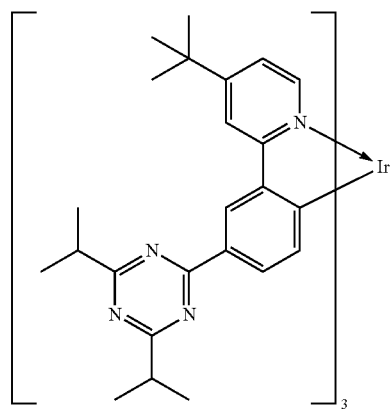

MN-2

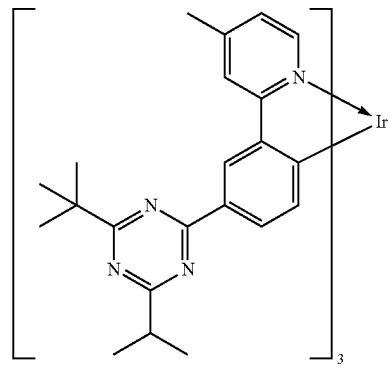

MN-3

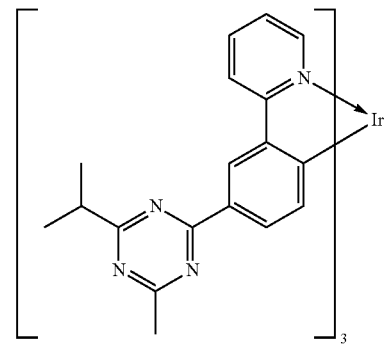

MN-4

[Chem. 9]

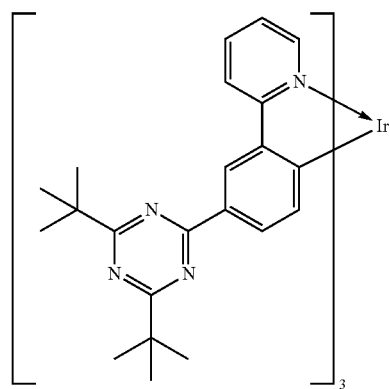

MN-5

MN-6
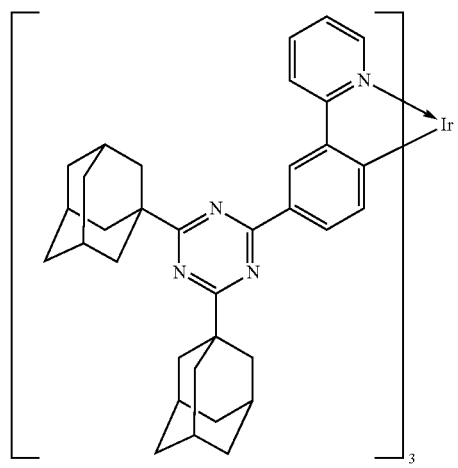
[Chem. 10]
MN-7
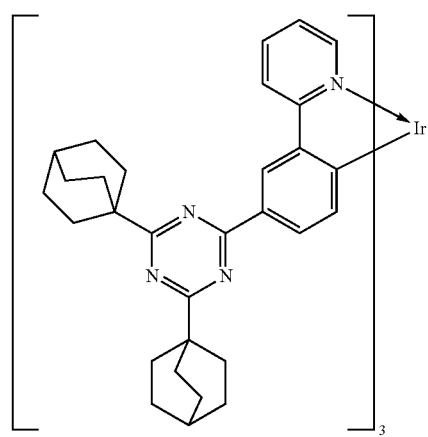
MN-8
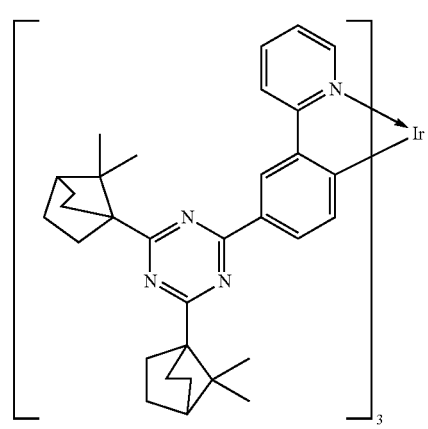
[Chem. 11]
MN-9
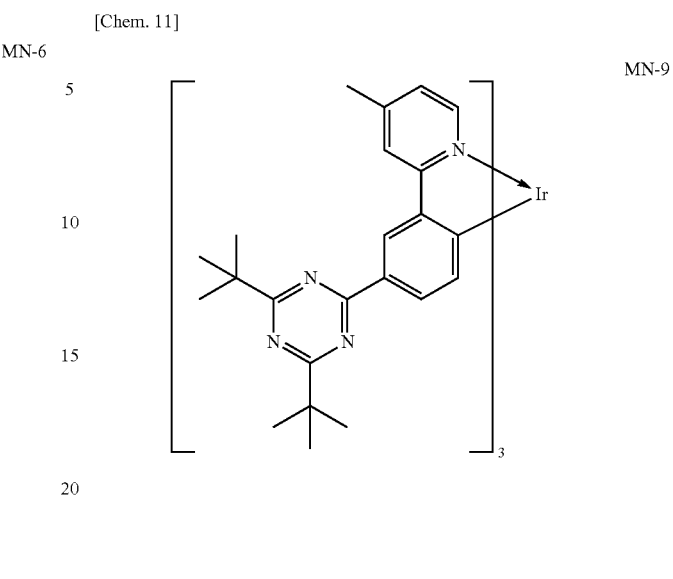
MN-10
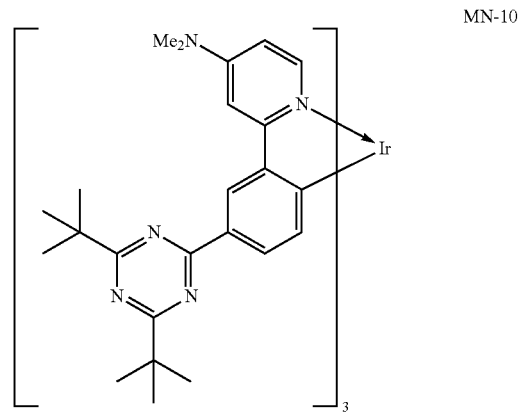
[Chem. 12]
MN-11
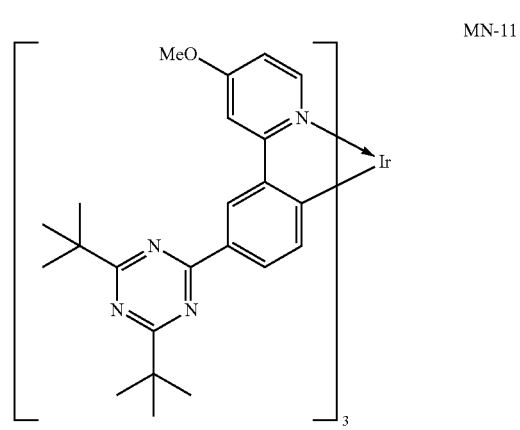

[Chem. 14]
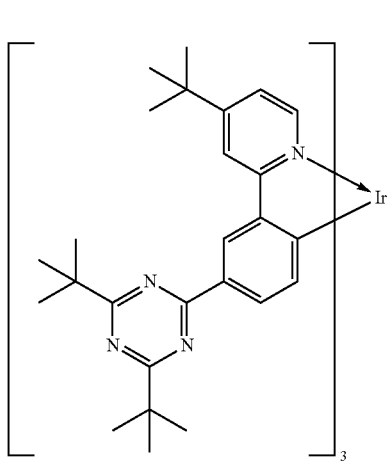
MN-12
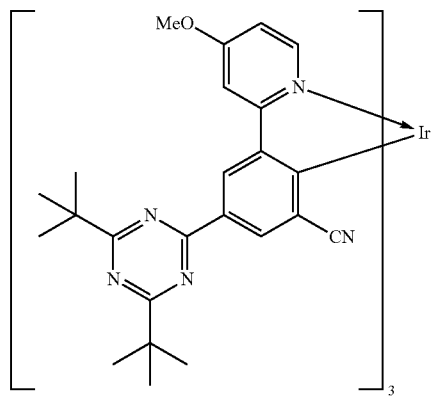
MN-13
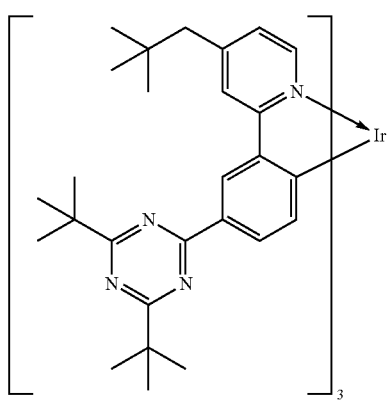
MN-14
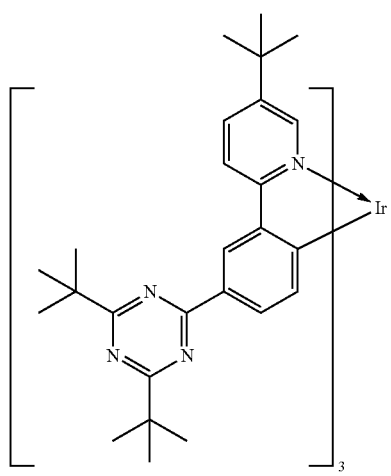
MN-15
MN-16
[Chem. 15]
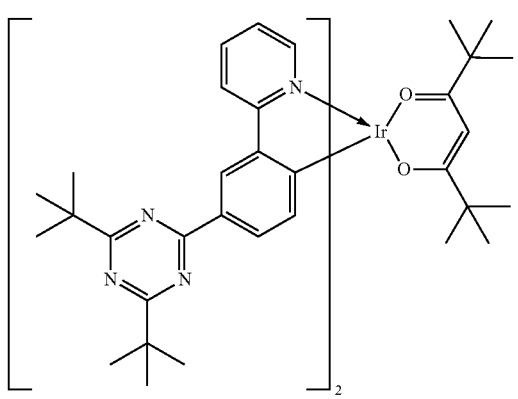
MN-17

[Chem. 16]

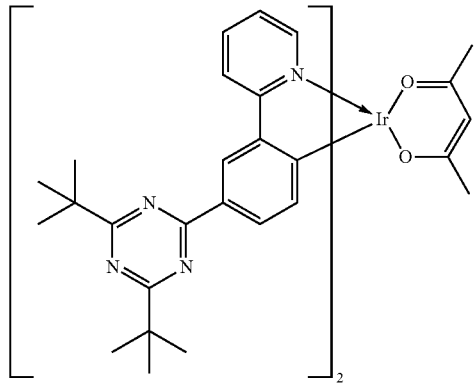
MN-18

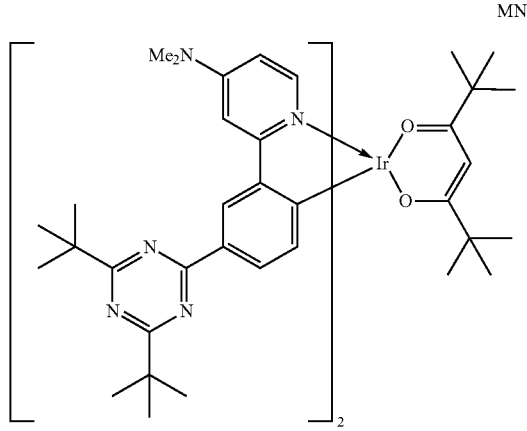
MN-19

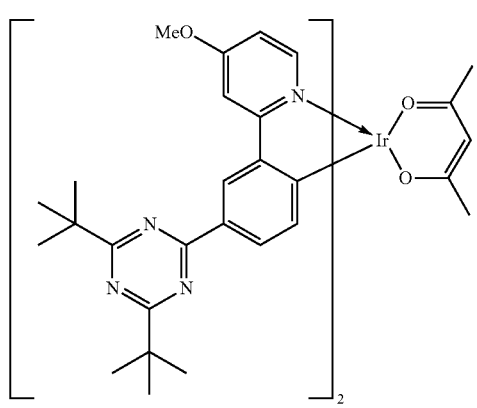
MN-20

[Chem. 17]

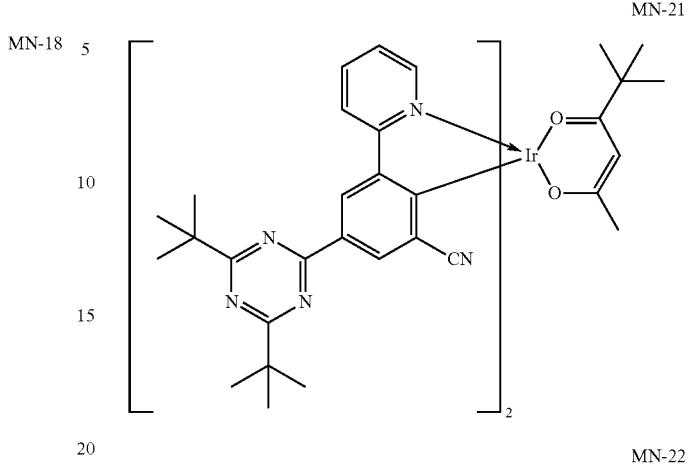
MN-21

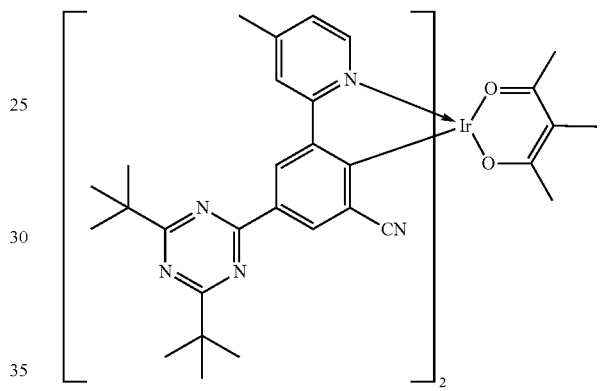
MN-22

Properties of MN-1 to MN-4

For each of the exemplified compounds, an alkyl group corresponding to each of $R_1$ and $R_2$ in formula (1) is a primary or secondary alkyl group. The primary or secondary alkyl group has a lower molecular weight than that of a tertiary alkyl group.

Properties of MN-5 and MN-22

For each of the exemplified compounds, an alkyl group corresponding to each of $R_1$ and $R_2$ in formula (1) is a tertiary alkyl group. The tertiary alkyl group has a large excluded volume and thus suppresses the coordinating ability of the lone pairs of the nitrogen atoms of the triazine ring. This can lead to not only a higher purity and higher yield of the compound in the synthesis of the compound but also the suppression of the intermolecular interaction to provide the effect of inhibiting the occurrence of the concentration quenching and to provide improvement in sublimability.

Properties of MN-17 to MN-22

MN-17 to MN-22 are specific examples of the iridium complex represented by formula (2) and each have a substituted or unsubstituted acetylacetonate ligand. These are easily produced and provide cost advantages.

As illustrated above, exemplary compounds are described. Furthermore, the introducing a substituent into the basic skeleton of the iridium complex according to aspects of the present invention can result in blue-to-green light emission.

Description of Organic Light-Emitting Device

An organic light-emitting device according to aspects of the present invention will be described below.

The organic light-emitting device according to aspects of the present invention includes an anode, a cathode, which are a pair of electrodes, and an organic compound layer provided between the electrodes. The organic compound layer contains the iridium complex represented by formula (1) or (2). The organic light-emitting device is defined as a device in which excitons of the luminous iridium complex in the organic compound layer are generated by injecting carriers from the anode and the cathode and in which light is released when the excitons return to the ground state.

In the case where the organic compound layer serves as a light-emitting layer, the light-emitting layer may consist of the iridium complex according to aspects of the present invention or may contain another component.

In the case where the light-emitting layer may partially contain the iridium complex according to aspects of the present invention, the iridium complex according to aspects of the present invention may be a main component in the light-emitting layer or may be an auxiliary component.

The term "main component" used here indicates a component having the highest proportion in weight among compounds contained in the light-emitting layer. The term "auxiliary component" indicates a compound having a lower proportion in weight than that of the main component.

A material serving as the main component can also be referred to as the host material.

A material serving as the auxiliary component is a dopant (guest material). Examples of another auxiliary component include emission assisting materials and electron injection material.

In the case where the iridium complex according to aspects of the present invention is used as the guest material, the concentration of the guest material is preferably in the range of 0.01% by weight to 20% by weight and more preferably 0.5% by weight to 10% by weight with respect to the host material.

The inventors have conducted various studies and have found that an element containing the iridium complex represented by formula (1) or (2) according to aspects of the present invention as the host material or the guest material, in particular, the guest material, in the light-emitting layer has high-efficiency and high-luminance optical output.

An example of the organic light-emitting device containing the iridium complex according to aspects of the present invention will be described below.

The organic light-emitting device containing the iridium complex according to aspects of the present invention may have a structure in which an anode, a light-emitting layer, and a cathode are provided, in that order, on a substrate. Furthermore, the organic light-emitting device may have a structure in which an anode, a hole transport layer, an electron transport layer, and a cathode are provided, in that order, on a substrate. In this case, light is emitted from the interface between the hole transport layer and the electron transport layer; hence, the hole transport layer and the electron transport layer serve as a light-emitting layer.

In addition, the organic light-emitting device may have a structure in which an anode, a hole transport layer, a light-emitting layer, an electron transport layer, and a cathode are provided, in that order, on a substrate. Moreover, the organic light-emitting device may have a structure in which an anode, a hole injection layer, a hole transport layer, a light-emitting layer, an electron transport layer, and a cathode are provided, in that order, on a substrate. Furthermore, the organic light-emitting device may have a structure in which an anode, a hole transport layer, a light-emitting layer, a hole/exciton blocking layer, an electron transport layer, and a cathode are provided, in that order, on a substrate. These five examples of the multilayer structures are very basic device structures. The structure of the organic light-emitting device containing the iridium complex according to aspects of the present invention is not limited thereto. The organic light-emitting device may have a layer structure selected from various layer structures, for example, a structure in which an insulating layer is provided between an electrode and an organic compound layer, a structure in which an adhesive layer or an interference layer is provided, and a structure in which an electron transport layer or a hole transport layer is formed of two sublayers having different ionization potentials.

The iridium complex represented by formula (1) or (2) according to aspects of the present invention may be used as an organic compound layer of the light-emitting device in any layer structure.

Here, the organic light-emitting device may contain the iridium complex according to aspects of the present invention together with an additional compound, as needed. Examples of the additional compound include a hole-injecting compound, a hole-transporting compound, a host compound, which is a host material, a light-emitting compound, an electron-injecting compound, and an electron-transporting compound. These compounds are known low-molecular-weight or high-molecular-weight compounds.

Examples of these compounds are described below.

The hole-injecting compound or hole-transporting compound can be a material having a high hole mobility. Non-limiting examples of the low-molecular-weight material and the high-molecular-weight compound having the capability of injecting or transporting holes include triarylamine derivatives, phenylenediamine derivatives, stilbene derivatives, phthalocyanine derivatives, porphyrin derivatives, poly(vinylcarbazole), polythiophene, and other conductive polymers.

Examples of the host compound include AM1 to AM10 illustrated below. In addition to these compounds, examples thereof include, but are not limited to, fused-ring compounds, such as fluorene derivatives and carbazole derivatives; organic aluminum complexes such as tris(8-quinolinolato) aluminum; organic zinc complexes; triphenylamine derivatives; and polymer derivatives, such as polyfluorene derivatives and polyphenylene derivatives.

[Chem. 18]

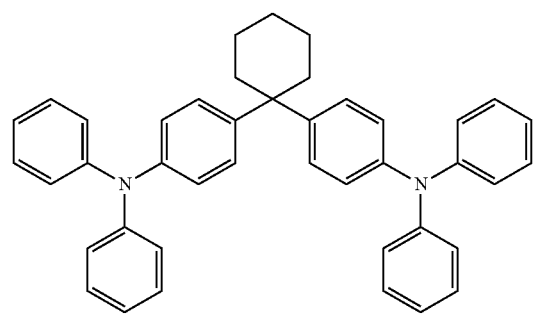

AM-1

AM-2
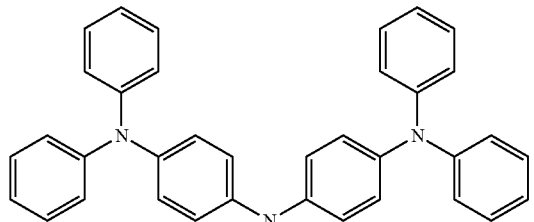

AM-3
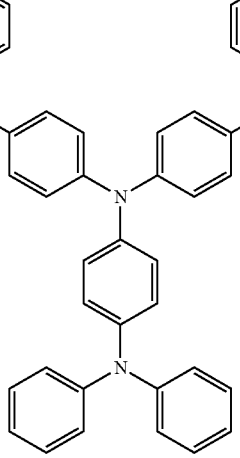

AM-4
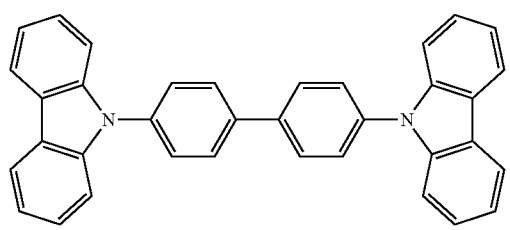

AM-5
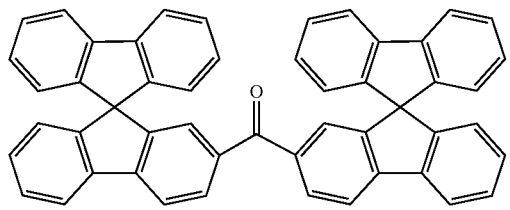

AM-6
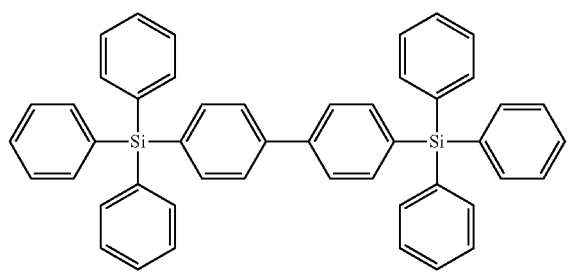

AM-7
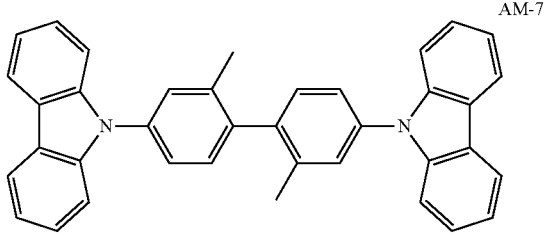

AM-8
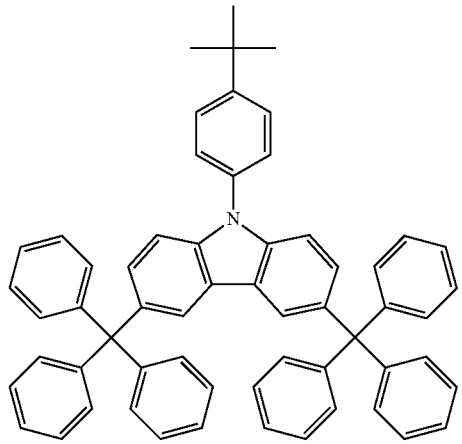

AM-9
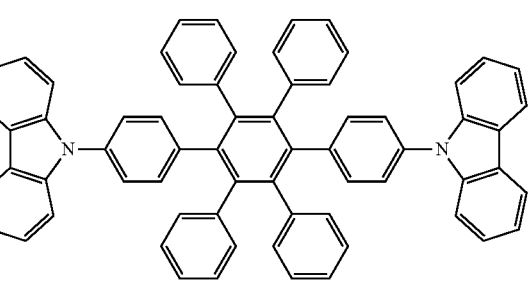

AM-10
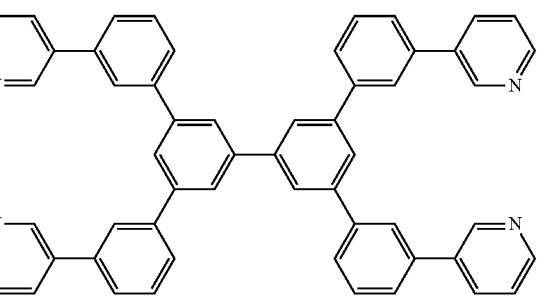

The electron-injecting compound or the electron-transporting compound is selected in view of, for example, the hole mobility of the hole-injecting compound or the hole-transporting compound. Examples of the compound having capability of injecting or transporting electrons include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The anode may be composed of a material having a higher work function. Examples thereof include elemental metals, such as gold, platinum, silver, copper, nickel, palladium, cobalt, selenium, vanadium, and tungsten; alloys thereof; and metal oxides, such as tin oxide, zinc oxide, indium oxide, indium tin oxide (ITO), and indium zinc oxide. Furthermore, conductive polymers, such as polyaniline, polypyrrole, polythiophene, and poly(phenylene sulfide), may be used. These electrode materials may be used alone or in combination. The anode may have a single-layer structure or a multilayer structure.

The cathode may be composed of a material having a lower work function. Examples of the material include elemental metals, such as alkali metals, e.g., lithium, alkaline-earth meals, e.g., calcium, aluminum, titanium, manganese, silver, lead, and chromium; and alloys thereof. Examples of the alloys that can be used include magnesium-silver, aluminum-lithium, and aluminum-magnesium. Metal oxides such as indium tin oxide (ITO) may be used. These electrode materials may be used alone or in combination. The cathode may have a single-layer structure or a multilayer structure.

In the organic light-emitting device according to aspects of the present invention, a layer containing the iridium complex according to aspects of the present invention and another layer composed of an organic compound are formed by a method described below. In general, a thin film may be formed by vacuum evaporation, ionized evaporation, sputtering, or a method using plasma. Alternatively, a thin film may be formed by a known coating method, e.g., spin coating, dipping, casting, the Langmuir-Blodgett (LB) technique, or an ink-jet method, using a solution of a material dissolved in an appropriate solvent. Here, the formation of the layer by, for example, vacuum evaporation or the coating method, is less likely to cause crystallization or the like, resulting in excellent stability with time. Furthermore, in the case of forming a film by a coating method, the film may be formed in combination with an appropriate binder resin.

Non-limiting examples of the binder resin include polyvinyl carbazole resins, polycarbonate resins, polyester resins, ABS resins, acrylic resins, polyimide resins, phenolic resins, epoxy resins, silicone resins, and urea resins. These binder resins in the form of homopolymers or copolymers may be used alone or in combination as a mixture. If necessary, they can be used together with a well-known additive such as a plasticizer, an antioxidant, and an ultraviolet absorber.

Application of Organic Light-Emitting Device

The organic light-emitting device according to aspects of the present invention may be used for, for example, a display, a lighting apparatus, an exposing light source of an image forming apparatus using an electrographic method, or a backlight of a liquid crystal display.

The display is provided with a display unit that includes the organic light-emitting device according to aspects of the present invention. The display can display an object with the organic light-emitting device.

The display unit includes a pixel. The pixel may include the organic light-emitting device according to aspects of the present invention. The display may be used as an image display apparatus of, for example, a personal computer.

The display may be used for a display unit of an image pick-up apparatus, for example, a digital camera or a digital video camera. The image pick-up apparatus includes the display unit and an image pick-up unit configured to pick-up an image, the image pick-up unit including an image pick-up optical system.

The display may include the display unit and an image input unit. The image input unit serves as, for example, the image pick-up optical system, a light detecting unit such as a CCD sensor, a unit configured to receive information from, for example, a memory card, or a scanner. An example of an apparatus including a display unit having the organic light-emitting device according to aspects of the present invention is a multifunction image forming apparatus having a scanner function and an image output function in addition to the digital camera or the digital video camera described above. The multifunction image forming apparatus may be an image forming apparatus using an ink-jet method or an image forming apparatus using an electrographic method.

Next, the display including the organic light-emitting device according to aspects of the present invention will be described.

Figure 5:
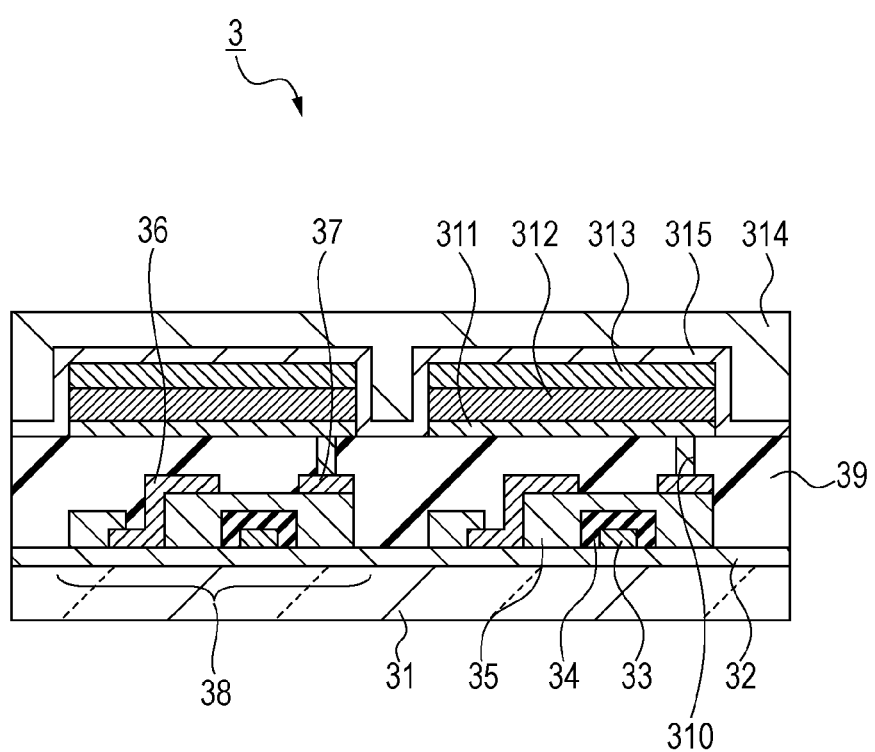
FIG. 5 is a schematic cross-sectional view illustrating organic light-emitting devices and TFT elements, which are switching elements, connected to the respective organic light-emitting devices.

FIG. 5 is a cross-sectional view illustrating organic light-emitting devices, serving as pixels, according to aspects of the present invention and switching elements connected to the respective organic light-emitting devices. In this figure, the switching elements are TFT elements. Alternatively, the switching elements may be MIM elements.

The display 3 includes a substrate 31 composed of, for example, glass, and a dampproofing film 32 formed on the substrate 31, the dampproofing film 32 being configured to protect the TFT elements or the organic compound layers. Reference numeral 33 denotes a gate electrode composed of a metal such as Cr. Reference numeral 34 denotes a gate insulating film. Reference numeral 35 denotes a semiconductor layer.

TFT elements 38 each include the semiconductor layer 35, a drain electrode 36, and a source electrode 37. The TFT elements 38 are overlaid with an insulating film 39. An anode 311 of each organic light-emitting device is connected to a corresponding one of the source electrodes 37 through a corresponding one of contact holes (through-holes) 310.

Although organic compound layers 312 each have a multilayer structure, each of the organic compound layers 312 is illustrated as a single layer, for the sake of simplicity. Cathodes 313 are overlaid with a first protective layer 314 and a second protective layer 315 configured to suppress the degradation of the organic light-emitting devices.

The luminance of each of the organic light-emitting devices is controlled by a corresponding one of the TFT elements. In the case where the plural organic light-emitting devices are arranged in one plane, the luminance can be controlled for each device, thereby displaying an image.

EXAMPLES

Examples will be described below. The present invention is not limited to the examples.

Example 1

Synthesis of Exemplary Compound MN-18

Exemplary compound MN-18 is synthesized from compound XX-4 that prepared from compound XX-3 as described below.

Synthesis of Intermediate XX-3

Intermediate XX-1 was synthesized according to, for example, Macromolecules 2003, 36, 9721-9730 or J. Org. Chem. 2004, 69, 6766-6771.

Intermediate XX-2 was synthesized according to, for example, Angew. Chem. Int. Ed., 2008, 47, 8246-8250.

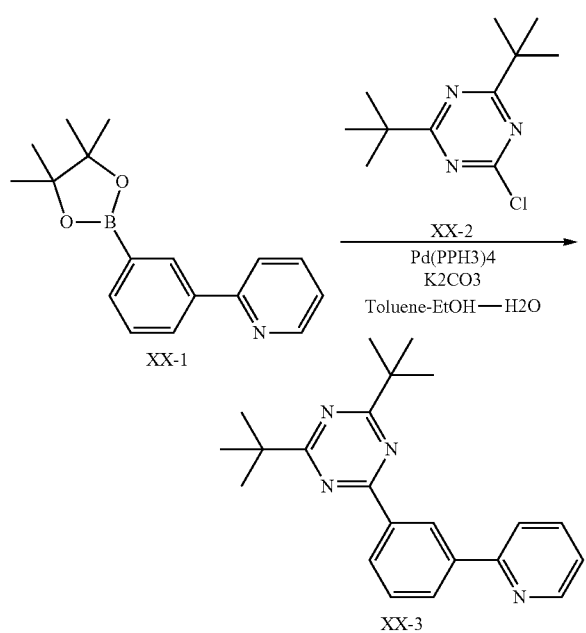

Reagents, solvents, and so forth described below were charged into a 300-mL reactor.
XX-1: 3 g (10.7 mmol)
XX-2: 3.4 g (14.9 mmol)
Toluene: 100 mL
2 N Aqueous solution of sodium carbonate: 100 mL
Ethanol: 50 mL
Tetrakis(triphenylphosphine)palladium[0]: 244 mg (0.16 mmol)

The resulting reaction solution was heated to 90° C. and stirred at this temperature for 5 hours. After cooling to room temperature, extraction was performed with toluene (100 mL×3). The organic layer was dried over magnesium sulfate. The drying agent was filtered off. After the resulting filtrate was concentrated, the residue was purified by silica gel column chromatography (mobile phase: chloroform) to give 3.1 g (8.9 mmol, 84% yield) of target compound XX-3.

Analysis by matrix-assisted laser desorption ionization-time-of-flight mass spectrometry (MALDI-TOF MS) demonstrated that M+ of this compound was found to be 346.

Furthermore, the structure of this compound was determined by NMR measurement.

$^1$H NMR (CDCl$_3$, 500 MHz) δ (ppm): 9.13 (s, 1H), 8.75 (d, 1H), 8.65 (d, 1H), 8.24 (d, 1H), 7.86-7.80 (m, 2H), 7.61 (t, 1H), 7.28 (m, 1H), 1.46 (s, 18H).

Synthesis of Intermediate XX-4

Into a 300-mL three-necked flask, 578 mg (1.64 mmol) of iridium(III) chloride, 1.25 g (3.6 mmol) of XX-3, 15 mL of ethoxyethanol, and 5 mL of distilled water were charged. The resulting mixture was stirred for 30 minutes at room temperature under a stream of nitrogen and then another 8 hours at 105° C. The reaction mixture was cooled to room temperature. The resulting precipitates were collected by filtration. The precipitates were washed with water and then methanol. The precipitates were dried in vacuo to give 1.1 g (73% yield) of XX-4.

Furthermore, the structure of this compound was determined by NMR measurement.

$^1$H NMR (CDCl$_3$, 500 MHz) δ (ppm): 9.31 (d, 1H), 8.74 (s, 1H), 8.12 (d, 1H), 7.89 (t, 1H), 7.78 (d, 1H), 6.89 (t, 1H), 6.06 (d, 1H), 1.35 (s, 18H).

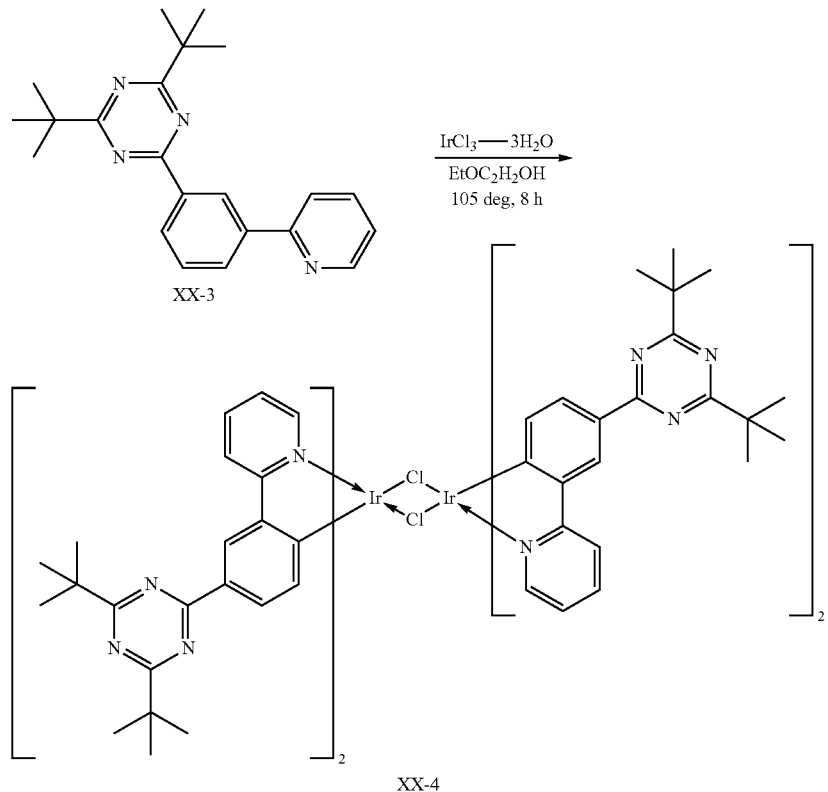

Synthesis of Exemplary Compound MN-18

Into a 300-mL three-necked flask, 100 mL of ethoxyethanol, 300 mg (0.163 mmol) of XX-4, 163 mg (1.63 mmol) of acetylacetone, and 228 mg (2.1 mmol) of sodium carbonate were charged. The resulting mixture was stirred at room temperature under a stream of nitrogen and then another 8 hours at 105° C. The reaction mixture was cooled to room temperature. The resulting precipitates were collected by filtration and then washed with water to give 220 mg (68% yield) of MN-18.

Analysis by matrix-assisted laser desorption ionization-time-of-flight mass spectrometry (MALDI-TOF MS) demonstrated that M+ of this compound was found to be 982.

Furthermore, the structure of this compound was determined by NMR measurement.

$^1$H NMR (CDCl$_3$, 500 MHz) δ (ppm): 8.77 (s, 2H), 8.54 (d, 2H), 8.07 (d, 2H), 7.90-7.83 (m, 4H), 7.22 (t, 2H), 6.42 (d, 2H), 5.24 (s, 1H), 1.80 (s, 6H), 1.37 (s, 36H).

FIG. 1 is a graph illustrating emission spectra of exemplary compound MN-18 and Ir(PPy)$_2$acac, which is a comparative compound, represented by the following structural formula.

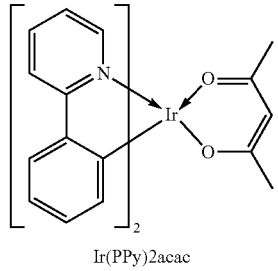

[Chem. 22]

Ir(PPy)2acac

The long-wavelength component of the iridium complex according to aspects of the present invention is reduced compared with that of Ir(PPy)$_2$acac.

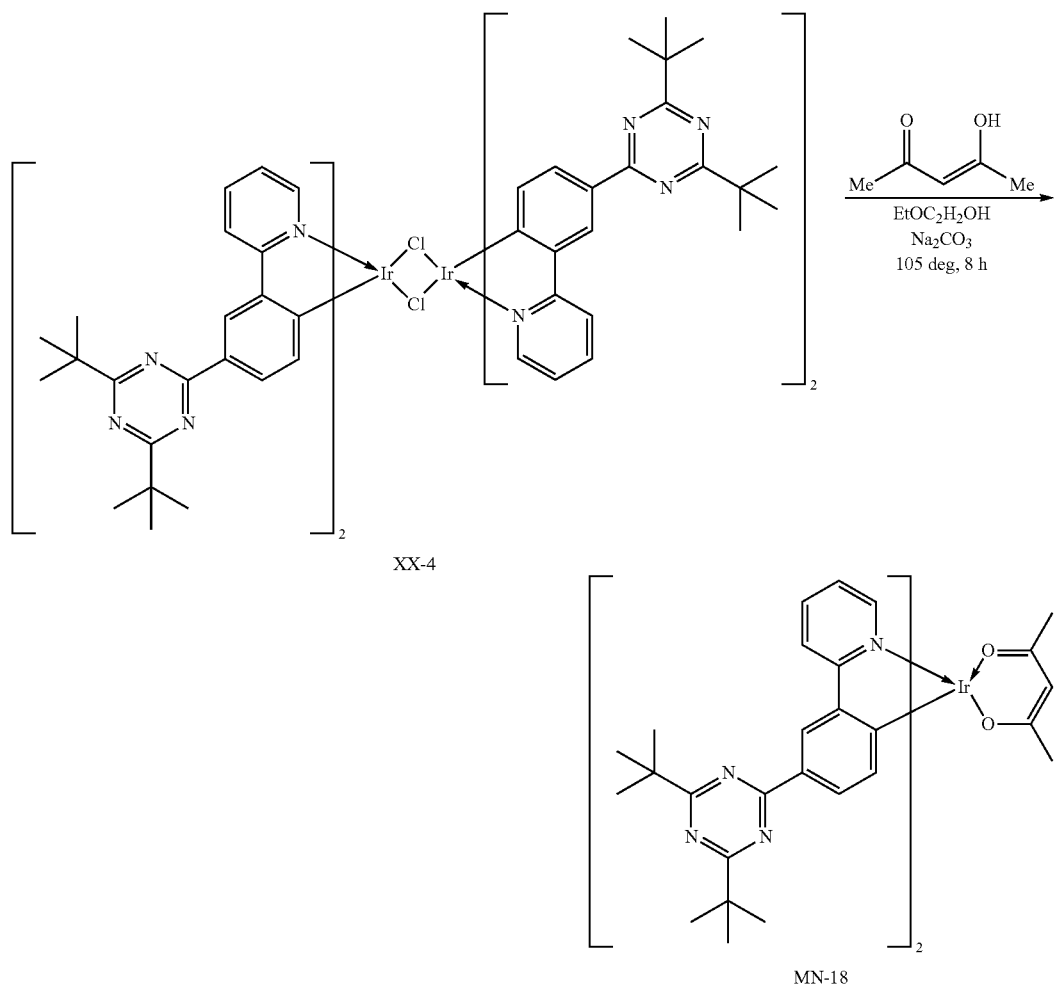

[Chem. 21]

Measurement of the photoluminescence spectrum of a 1×10$^{-5}$ mol/L toluene solution of exemplary compound MN-18 using a fluorescence spectrophotometer (Model F-4500, manufactured by Hitachi, Ltd.) at an excitation wavelength of 450 nm demonstrated that the resulting spectrum had a maximum intensity at 493 nm.

Figure 2:
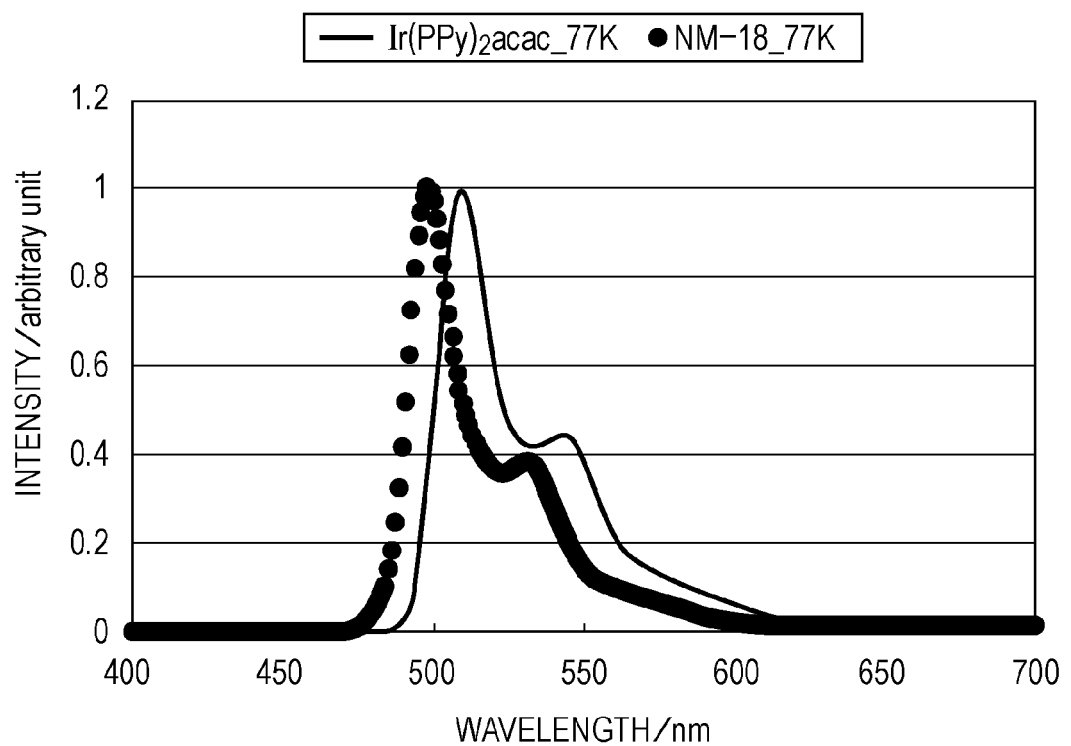
FIG. 2 illustrates emission spectra of exemplary compound MN-18 according to the embodiment and $Ir(PPy)_2acac$ according to the comparative example at 77 K.

FIG. 2 illustrates emission spectra of exemplary compound MN-18 and Ir(PPy)$_2$acac in toluene at 77 K.

In the emission spectra, a second peak of exemplary compound MN-18 had an intensity of 0.38, and a second peak of Ir(PPy)$_2$acac had an intensity of 0.44, with respect to the corresponding maximum emission intensity.

The foregoing results demonstrate that the compound according to aspects of the present invention is an excellent light-emitting material having a small second peak.

With respect to the emission quantum yield (Φ) in this example, when the emission quantum yield (Φ) of Ir(PPy)$_2$acac was 0.28, the emission quantum yield (Φ) of exemplary compound MN-18 was 0.43.

Thus, exemplary compound MN-18 has an excellent skeleton from the viewpoint of achieving a good emission yield.

In toluene glass (at 77 K), the phosphorescence lifetime of Ir(PPy)$_2$acac was 3.4 μsec, and the phosphorescence lifetime of exemplary compound MN-18 was 2.0 μsec. A short emission lifetime indicates a high radiative rate. Thus, the iridium complex according to aspects of the present invention has excellent emission characteristics.

Example 2

Organic Light-Emitting Device Containing MN-18 Serving as Light-Emitting Material In this example, an organic light-emitting device having a structure of anode/hole injection layer/hole transport layer/light-emitting layer/electron transport layer/cathode stacked in that order was produced.

On a glass substrate, a 100-nm-thick ITO was formed by patterning. A chloroform solution of MM-1, which is illustrated below, was applied by spin coating on the ITO substrate to form a hole injection layer having a thickness of 30 nm. Then organic compound layers and electrode layers described below were continuously formed thereon by vacuum evaporation using resistance heating in a vacuum chamber at $10^{-5}$ Pa. In this case, the device was produced so as to have an area of the facing electrodes of 3 mm$^2$.

Hole transport layer (20 nm) MM-1
Light-emitting layer (40 nm) host: MM-2, guest: exemplary compound MN-18 (weight ratio: 10%)
Electron transport layer (30 nm) MM-3
Metal electrode layer 1 (1 nm) LiF
Metal electrode layer 2 (150 nm) Al

[Chem. 23]

MM-1

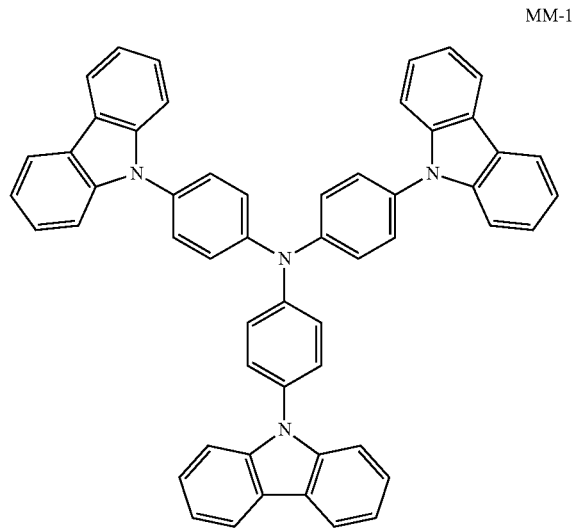

-continued

MM-2

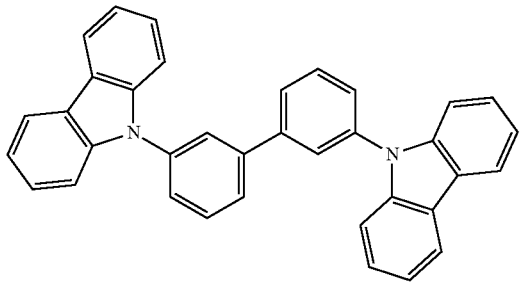

MM-3

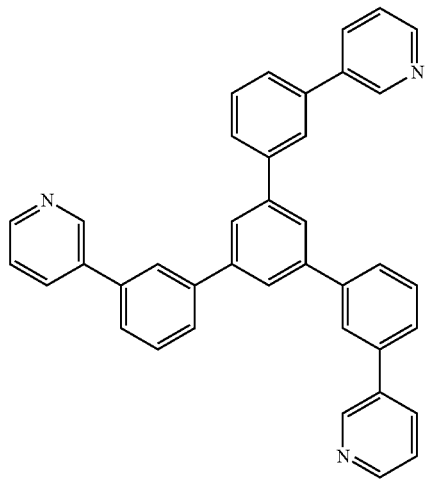

With respect to the properties of the EL device, the current-voltage characteristic was measured with a microammeter (Model 4140B, manufactured by Hewlett-Packard Company), and the emission luminance was measured with a luminance meter (Model BM7, manufactured by Topcon Corporation).

When a current of 5 mA/cm$^2$ was applied, the luminance was 48 cd/A. In this case, the external quantum efficiency ($\Phi_{exe}$) was 15%. The results demonstrated that light was emitted with high efficiency.

Example 3

Synthesis of Exemplary Compound MN-5

This example relates to the synthesis of exemplary compound MN-5, which is one of the iridium complexes represented by formula (1).

Into a 50-mL two-necked flask, 100 mg (0.102 mmol) of MN-18 and 1 g (2.886 mmol) of XX-3 were charged. The resulting mixture was stirred at about 200° C. for 8 hours under a stream of nitrogen. After the reaction mixture was cooled to room temperature, methanol was added thereto. The resulting precipitates were collected by filtration. The precipitates were purified by silica gel column chromatography using toluene as an eluent to give 85 mg (68% yield) of MN-5 as a meridional isomer.

Analysis by matrix-assisted laser desorption ionization-time-of-flight mass spectrometry (MALDI-TOF MS) demonstrated that M+ of this compound was found to be 1228.

Furthermore, the structure of this compound was determined by NMR measurement.

$^1$H NMR (CDCl$_3$, 500 MHz) δ (ppm): 8.99 (s, 1H), 8.94 (s, 1H), 8.91 (s, 1H), 8.19-8.12 (m, 4H), 8.08-8.01 (m, 4H), 7.90-7.83 (m, 4H), 7.74 (t, 1H), 7.68-7.58 (m, 3H), 7.16 (d, 1H), 6.94 (t, 1H), 6.79 (m, 3H), 6.62 (d, 1H), 1.40 (s, 52H).

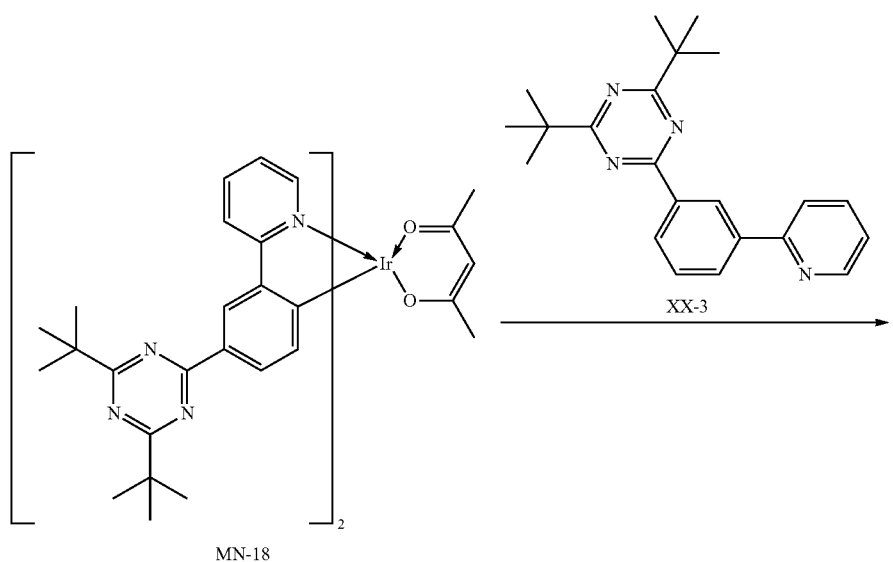

MN-18

XX-3

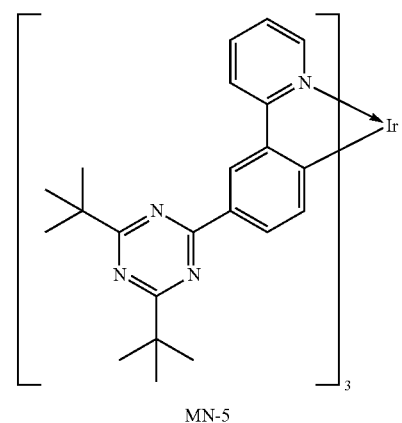

MN-5

Next, the photoisomerization of exemplary compound MN-5 will be described.

First, 130 mg of the meridional isomer of MN-5 was charged into a 100-mL Pyrex (registered trademark) test tube under an argon atmosphere and dissolved in 60 mL of DMSO. The resulting solution was irradiated with light from a medium pressure mercury lamp for 8 hours with the tube cooled with water.

The precipitated crystals were collected by filtration and washed with methanol. The crystals were dried in vacuo to give 120 mg (92% yield) of MN-5 as a facial isomer.

Analysis by matrix-assisted laser desorption ionization-time-of-flight mass spectrometry (MALDI-TOF MS) demonstrated that M+ of this compound was found to be 1228.

$^1$H NMR (CDCl$_3$, 400 MHz) δ (ppm): 8.91 (s, 3H), 8.11 (d, 3H), 8.03 (m, 3H), 7.70 (t, 3H), 7.59 (d, 3H), 7.07 (d, 3H), 6.95 (t, 3H), 1.40 (s, 54H).

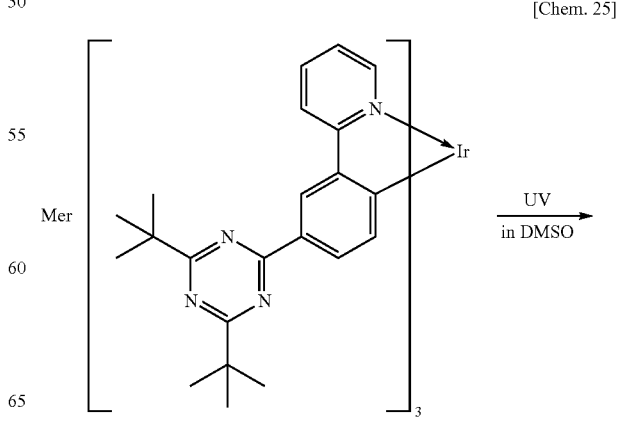

Mer → UV in DMSO

Figure 3:
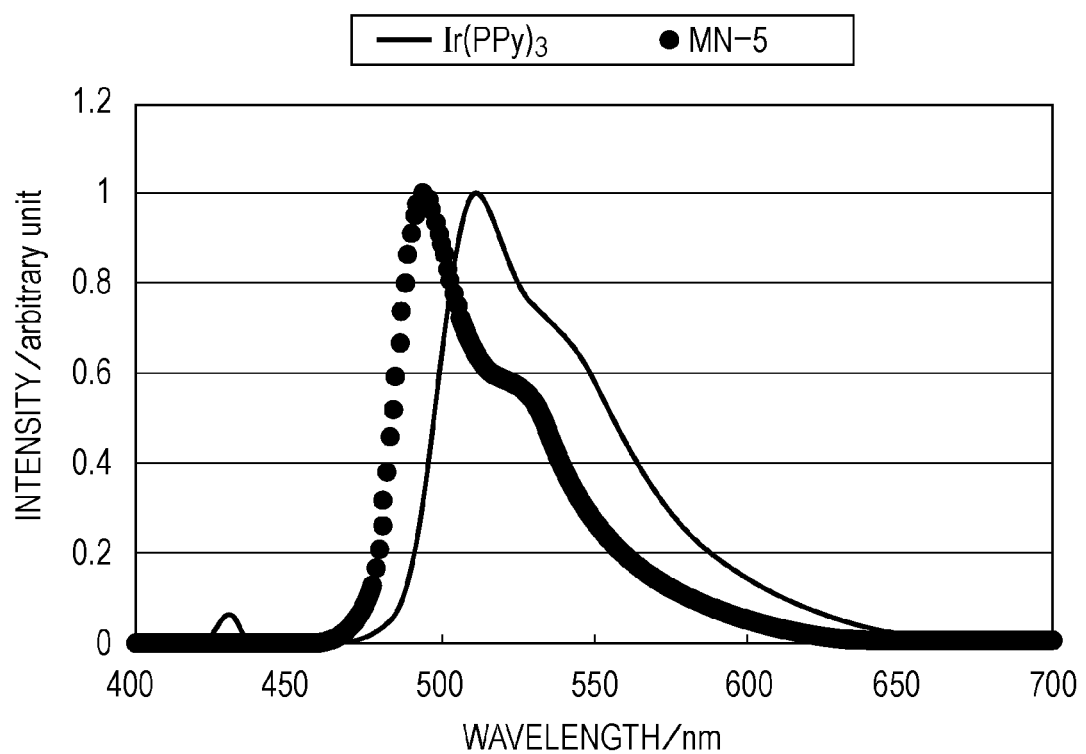
FIG. 3 illustrates emission spectra of exemplary compound MN-5 according to an embodiment and $Ir(PPy)_3$ according to a comparative example at room temperature.

Measurement of the photoluminescence spectrum of a 1×10$^{-5}$ mol/L toluene solution of the facial isomer of exemplary compound MN-5 at an excitation wavelength of 430 nm demonstrated that the resulting spectrum had a maximum intensity at 505 nm. The measurement was performed with a fluorescence spectrophotometer (Model F-4500, manufactured by Hitachi, Ltd). FIG. 3 illustrates emission spectra of the facial isomer of exemplary compound MN-5 and Ir(PPy)$_3$, which is a comparative compound.

The long-wavelength component of the facial isomer of exemplary compound MN-5 is reduced because a second peak of exemplary compound MN-5 is suppressed, as compared with that of Ir(PPy)$_3$.

Figure 4:
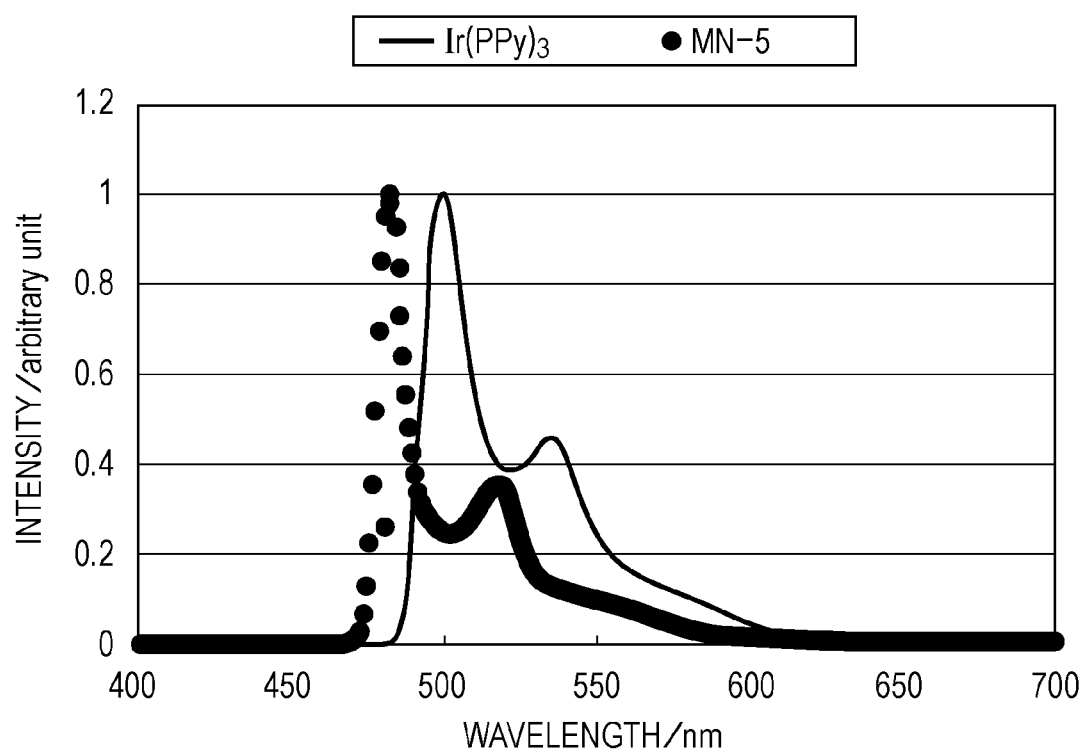
FIG. 4 illustrates emission spectra of exemplary compound MN-5 according to the embodiment and $Ir(PPy)_3$ according to the comparative example at 77 K.

FIG. 4 illustrates emission spectra of the facial isomer of exemplary compound MN-5 and Ir(PPy)$_3$ in toluene at 77 K.

In the emission spectra, the second peak of the facial isomer of exemplary compound MN-5 had an intensity of 0.35, and the second peak of Ir(PPy)$_3$ had an intensity of 0.44, with respect to the corresponding maximum emission intensity.

The foregoing results demonstrate that the compound according to aspects of the present invention is an excellent light-emitting material having a small second peak.

With respect to the emission quantum yield (4) in this example, when the emission quantum yield (4) of Ir(PPy)$_3$ was 0.4, the emission quantum yield (4) of the facial isomer of exemplary compound MN-5 was 0.4.

Thus, exemplary compound MN-5 has an excellent skeleton from the viewpoint of achieving a good emission yield.

In toluene glass (at 77 K), the phosphorescence lifetime of Ir(PPy)$_3$ was 4.0 μsec, and the phosphorescence lifetime of exemplary compound MN-5 was 2.0 μsec. A short emission lifetime indicates a high radiative rate. Thus, the iridium complex according to aspects of the present invention has excellent emission characteristics.

Example 4

Organic Light-Emitting Device Containing MN-5 Serving as Light-Emitting Material In this example, an organic light-emitting device having a structure of anode/hole injection layer/hole transport layer/light-emitting layer/electron transport layer/cathode stacked in that order was produced. The light-emitting layer contains the facial isomer of exemplary compound MN-5.

On a glass substrate, a 100-nm-thick ITO was formed by patterning. A chloroform solution of MM-1, which is illustrated below, was applied by spin coating on the ITO substrate to form a hole injection layer having a thickness of 30 nm. Then organic compound layers and electrode layers described below were continuously formed thereon by vacuum evaporation using resistance heating in a vacuum chamber at 10$^{-5}$ Pa. In this case, the device was produced so as to have an area of the facing electrodes of 3 mm$^2$.

Hole transport layer (20 nm) MM-1
Light-emitting layer (40 nm) host: MM-2, guest: exemplary compound MN-5 (facial isomer) (weight ratio: 10%)
Electron transport layer (30 nm) MM-3
Metal electrode layer 1 (1 nm) LiF
Metal electrode layer 2 (150 nm) Al

[Chem. 26]

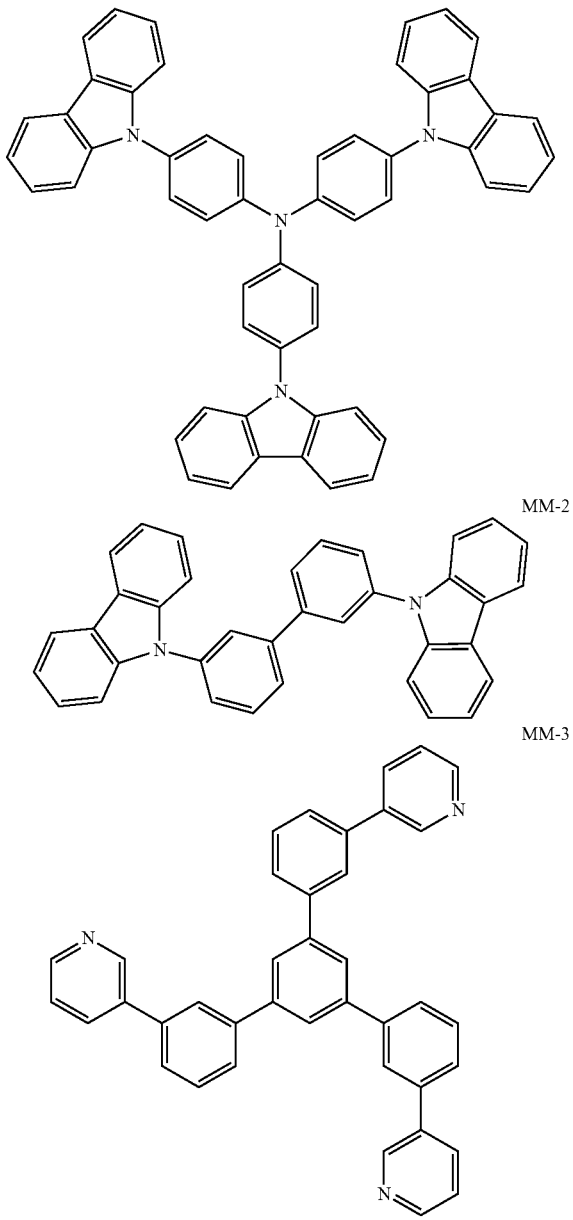

With respect to the properties of the EL device, the current-voltage characteristic was measured with a microammeter (Model 4140B, manufactured by Hewlett-Packard Company), and the emission luminance was measured with a luminance meter (Model BM7, manufactured by Topcon Corporation).

When a current of 5 mA/cm² was applied, the luminance was 50 cd/A. In this case, the external quantum efficiency ($\Phi_{exe}$) was 16%. The results demonstrated that light was emitted with high efficiency. Furthermore, green light having a peak wavelength of 498 nm was observed.

RESULTS AND DISCUSSION

The iridium complex according to aspects of the present invention is a new compound which has a high quantum yield and emits blue-to-green light. The use of the iridium complex for an organic light-emitting device results in a light-emitting device having satisfactory emission characteristics.

As described in the embodiments and the examples, aspects of the present invention provide the iridium complex having excellent emission characteristics and the organic light-emitting device having excellent emission characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-278968, filed Dec. 8, 2009, which is hereby incorporated by reference herein in its entirety.

The invention claimed is:

1. An iridium complex represented by formula (1):

[Chem. 1]

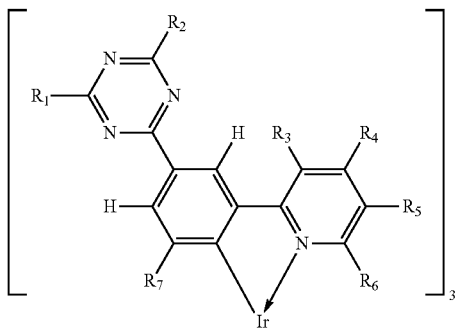

(1)

wherein
R₁ and R₂ each independently represent an alkyl group; and
R₃ to R₇ each independently represent one selected from a hydrogen atom, a cyano group, alkyl groups, alkoxy groups, and substituted amino groups.

2. The iridium complex according to claim 1, wherein each of R₁ and R₂ represent a tert-butyl group.

3. An organic light-emitting device comprising:
a cathode;
an anode; and
an organic compound layer provided between the cathode and the anode,
wherein the organic compound layer contains the iridium complex according to claim 1.

4. The organic light-emitting device according to claim 3, wherein the organic compound layer serves as a light-emitting layer.

5. A display comprising:
a plurality of pixels,
wherein each of the plural pixels includes the organic light-emitting device according to claim 3 and a switching element connected to the organic light-emitting device.

6. An iridium complex represented by formula (2):

[Chem. 2]

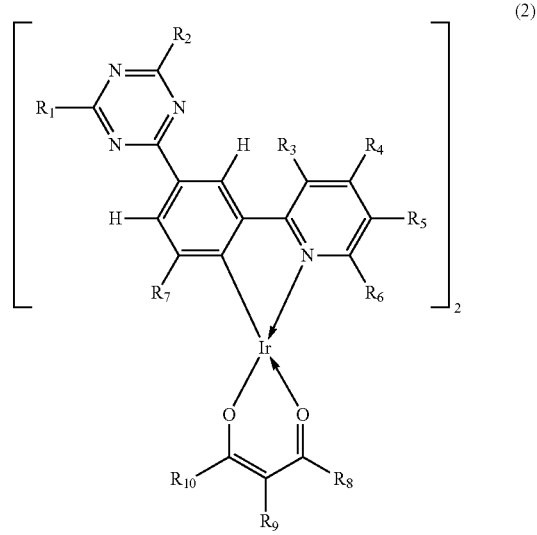

(2)

wherein R₁ and R₂ each independently represent an alkyl group;
R₃ to R₇ each independently represent one selected from a hydrogen atom, a cyano group, alkyl groups, alkoxy groups, and substituted amino groups; and
R₈ to R₁₀ each independently represent one selected from a hydrogen atom and alkyl groups.

7. The iridium complex according to claim 6, wherein each of R₁ and R₂ represent a tert-butyl group.

8. An organic light-emitting device comprising:
a cathode;
an anode; and
an organic compound layer provided between the cathode and the anode,
wherein the organic compound layer contains the iridium complex according to claim 6.

9. The organic light-emitting device according to claim 8, wherein the organic compound layer serves as a light-emitting layer.

10. A display comprising:
a plurality of pixels
wherein each of the plural pixels includes the organic light-emitting device according to claim 6 and a switching element connected to the organic light-emitting device.

* * * * *